(12) United States Patent
Lange et al.

(10) Patent No.: US 7,041,767 B2
(45) Date of Patent: May 9, 2006

(54) POLYSILOXANE POLYMERS, METHOD FOR THEIR PRODUCTION AND THE USE THEREOF

(75) Inventors: Horst Lange, Bochum (DE); Roland Wagner, Bonn (DE); Anita Witossek, Langenfeld (DE); Karl-Heinz Stachulla, Leverkusen (DE); Siegfried Teuber, Krefeld (DE); Albert Schnering, Köln (DE); Annette Möller, Leverkusen (DE); Martin Kropfgans, Odenthal (DE); Karl-Heinz Sockel, Leverkusen (DE); Don Firstenberg, Guilderland, NY (US)

(73) Assignee: GE Bayer Silicones GmbH & Co. KG, Erkrath (DE)

( * ) Notice: Subject to any disclaimer, the term of this patent is extended or adjusted under 35 U.S.C. 154(b) by 129 days.

(21) Appl. No.: 10/333,865

(22) PCT Filed: Jul. 17, 2001

(86) PCT No.: PCT/EP01/08695

§ 371 (c)(1),
(2), (4) Date: Nov. 12, 2003

(87) PCT Pub. No.: WO02/10259

PCT Pub. Date: Feb. 7, 2002

(65) Prior Publication Data
US 2004/0138400 A1 Jul. 15, 2004

(30) Foreign Application Priority Data
Jul. 27, 2000 (DE) .......................... 100 36 536

(51) Int. Cl.
D06M 15/643 (2006.01)
C08G 77/26 (2006.01)

(52) U.S. Cl. .............................. 528/28; 528/26; 528/31; 528/35; 252/8.61; 252/8.63

(58) Field of Classification Search ................ 252/8.61, 252/8.63; 528/26, 28, 31, 35
See application file for complete search history.

(56) References Cited

U.S. PATENT DOCUMENTS

| 4,833,225 A | 5/1989 | Schaefer et al. ............... 528/28 |
| 5,807,956 A * | 9/1998 | Czech .......................... 528/28 |
| 6,240,929 B1 | 6/2001 | Richard et al. ............. 132/202 |
| 6,242,554 B1 | 6/2001 | Busch et al. .................. 528/28 |

FOREIGN PATENT DOCUMENTS

| DE | 198 17 776 A | 10/1999 |
| EP | 0 282 720 A | 9/1988 |
| EP | 1 000 959 A | 5/2000 |
| FR | 2 535 730 A | 5/1984 |
| WO | WO 99 50338 A | 10/1999 |
| WO | WO 01 41720 A | 6/2001 |

* cited by examiner

Primary Examiner—Margaret G. Moore
Assistant Examiner—Marc S Zimmer
(74) Attorney, Agent, or Firm—Norris McLaughlin & Marcus PA

(57) ABSTRACT

The invention pertains to polysiloxane polymers, methods for their production, and their use as wash resistant hydrophilic softeners.

28 Claims, No Drawings

POLYSILOXANE POLYMERS, METHOD FOR THEIR PRODUCTION AND THE USE THEREOF

The invention relates to polysiloxane polymers preferably for applications as wash-resistant hydrophilic softening agents based on quaternary ammonium groups that contain siloxanes, a method for their production and their use preferably as softening agents.

Amino groups containing polysiloxane are known as textile softening agents from EP-A-0 441 530. The introduction of amino structures as lateral chains modified by ethylene oxide/propylene oxide units causes an improvement of the effect as described in U.S. Pat. Nos. 5,5918,80 and 5,650,529. Here the alkylene oxide units allow the specific adjustment of the hydrophilic-hydrophobic balance. The difficult esterification of amino alcohols with silicone-bonded carboxylic acid groups common during synthesis is disadvantageous for the building of compounds. In addition a difficulty lies in the softening characteristics, which are induced through the general comb-structure of the products. To eliminate these disadvantages, U.S. Pat. Nos. 5,807,956 and 5,981,681 suggests converting the $\alpha,\omega$-epoxy modified siloxanes with $\alpha,\omega$-amino functionalized alkyleneoxides and using these products as hydrophilic softeners.

To improve the substantivity, tests were conducted to introduce quaternary ammonium groups in alkyleneoxide-modified siloxanes. U.S. Pat. No. 5,625,024 discloses branched alkyleneoxide-modified polyquaternary polysiloxanes that were synthesized from $\alpha,\omega$-OH terminated polysiloxanes and trialkoxy silanes through condensation. The quaternary ammonium structure is introduced through silane, wherein the quaternary nitrogen atom is substituted by the alkyleneoxide units. Rigid comb-like alkyleneoxide-modified polyquaternary polysiloxanes are likewise described in U.S. Pat. No. 5,098,979. The hydroxyl groups from comb-like substituted polyethersiloxanes are converted with epichlorohydrin into the corresponding chlorohydrin derivatives. Finally a quaternation process occurs with tertiary amines. A disadvantage of this strategy is the necessary contact with epichlorohydrin and the relatively low reactivity of the chlorohydrin grouping during the quaternation.

Due to this, the hydroxyl groups of comb-like substituted polyether-siloxanes were esterified alternatively with chloroacetic acid. Through the carbonyl activation the concluding quaternation can be conducted more simply as already described, in U.S. Pat. Nos. 5,153,294 and 5,166,297.

WO 01/41719 and WO 01/41720 published after the priority date of this application describe quaternary polysiloxane compounds for use in cosmetic compositions.

The reaction of $\alpha,\omega$-di-epoxies with tertiary amines in the presence of acids results in $\alpha,\omega$-diquaternary siloxanes, which can be used for hair care purposes, and is already disclosed in DE-PS 37 19 086. A decrease in the ability of washing care substances out of the hair can be obtained if the $\alpha,\omega$-di-epoxies are reacted with di-tertiary amines in the presence of acids into long chains of polyquaternary polysiloxanes, as disclosed in EP-A-0 282 720. However the wash-resistance with regard to hair refers to the short-term effect of mainly water and very mild surfactants that do not irritate the skin, while the wash-resistant hydrophilic softeners for textiles must withstand the effects of concentrated surfactant solutions with a high ability to remove grease and dirt. Also aggravating is the fact that modern laundry detergents contain strong alkaline complexing agents, oxydatively acting bleaching agents and complex enzyme systems and that the fibers are often exposed to the effects for hours at high temperatures.

Due to this, a basically different approach is described in DE-OS 32 36 466. The reaction of OH-terminated siloxanes with quaternary ammonium structures containing alkoxysilanes results in reactive intermediate products, which should cross-link with suitable cross-linking agents such as trialkoxysilanes on the fiber surface into wash-resistant coatings. A significant disadvantage to this approach is that the stability of an aqueous finishing bath, which is required for several hours, cannot be guaranteed and unforeseen cross-linking reactions in the bath can occur even before textile finishing.

The described suggestions do not represent any satisfactory solutions to the problem of how to obtain the soft touch typical for progressive silicones and the distinctive hydrophilicity after the initial finishing of a textile material even when it is exposed to the effects of aggressive detergent formulations in the process of repeated washings if necessary at elevated temperatures.

Thus it is the objective of the invention to make polysiloxane compounds, in particular polyquaternary polysilicones, their manufacture and their use as wash-resistant hydrophilic softeners available while not exhibiting the disadvantages of the state of the art.

The polysiloxane compounds pursuant to the invention, in particular the polyquaternary silicones, should provide a soft touch typical for silicone and a distinctive hydrophilism to the textiles after appropriate application, and this characteristic should not be lost even after exposure to detergent formulations during repeated washings, if necessary at elevated temperatures.

This task is resolved with polysiloxane polymers with the repetition units

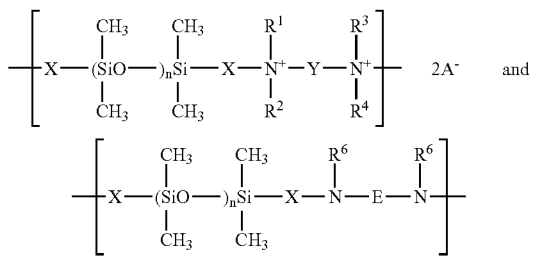

wherein

X is a bivalent hydrocarbon radical with at least 4 carbon atoms, which contains a hydroxyl group and which can be interrupted by an oxygen atom, and the groups X in the repetition units can be the same or different, Y is a bivalent hydrocarbon radical with at least 2 carbon atoms, which can contain a hydroxyl group and which can be interrupted by one or more oxygen or nitrogen atoms, preferably one oxygen atom or one nitrogen atom, $R^1$, $R^2$, $R^3$ and $R^4$ are the same or different and represent alkyl radicals with 1 to 4 carbon atoms or benzyl radicals or the radicals $R^1$ and $R^3$ or $R^2$ and $R^4$ can be components of a bridging alkylene radical, $R^6$ is H or an alkyl radical with 1 to 20 carbon atoms, which can be oxygen-substituted, E is the structure —B—O—(EOx)$_v$(POx)$_w$—B—, wherein EOx is an ethyleneoxide unit and POx a propyleneoxide unit, and B is linear or branched $C_2$ to $C_6$ alkylene, v is 0 to 200, w is 0 to 200, v+w corresponds to ≧1,
n is 2 to 1000, wherein n can be the same or different in the repetition units,
A⁻ represents an inorganic or organic anion.

The polysiloxane compounds pursuant to the invention are linear or cyclic polysiloxane polymers.

When linear polysiloxane polymers are involved, the terminal groups are usefully selected from

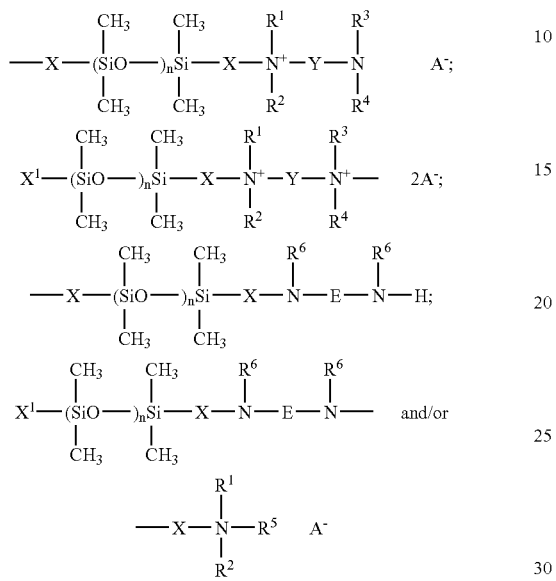

wherein X, $R^1$, $R^2$, $R^3$, $R^4$, $R^6$, Y, E, A* and n are defined as described above, $X^1$ is a hydrocarbon radical with at least 4 carbon atoms, which contains an epoxy group or an epoxy group opened with alcohols, water or amines, and which can be interrupted by an oxygen atom, and
$R^5$ is an alkyl radical with 1 to 20 carbon atoms, and
wherein the terminal groups X in the terminal groups, respectively, bind to the terminal nitrogen atoms of the repetition units and the terminal nitrogen atoms in the terminal groups, respectively, bind to the terminal groups X of the repetition units.

The first four terminal groups mentioned above hereby result from the bisamines used in production and described below, while the last terminal group results from a monoamine that may possibly be added during production.

The epoxy group mentioned above in the definition of X' is preferably a terminal epoxy group. In a particularly preferred version the group X' is selected from the following formulas:

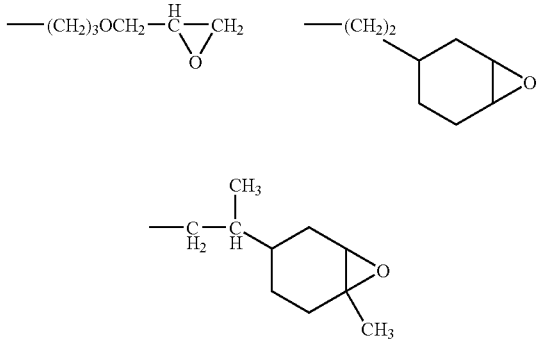

as well as epoxy structures thereof opened with alcohols, water or amines. Opening with alcohols results in radicals substituted with a hydroxyl group and an ether group, opening with water results in radicals substituted with two hydroxyl groups, and opening with amines results in hydroxylamine radicals. This is inherently known to the expert.

A preferred embodiment of the polysiloxane polymers pursuant to the invention involves cyclic polyquaternary polysiloxane polymers of the general formula (I)

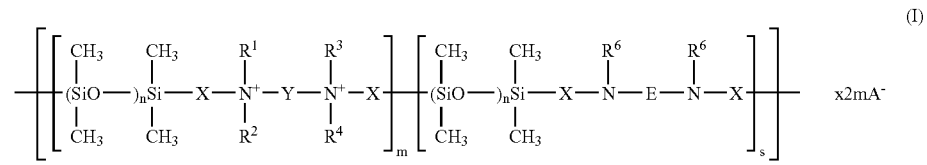

and/or linear compounds of the general formula (II)

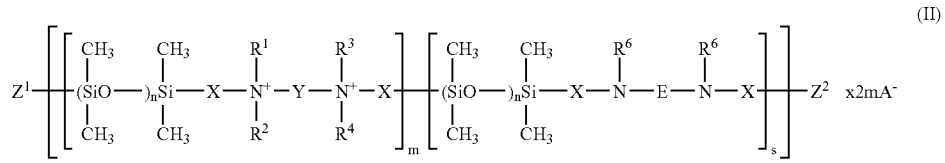

wherein
X is a bivalent hydrocarbon radical with at least 4 carbon atoms, which contains a hydroxyl group and which can be interrupted by an oxygen atom,
Y is a bivalent hydrocarbon radical with at least 2 carbon atoms, which can contain a hydroxyl group and which can be interrupted by one or more oxygen or nitrogen atoms,
$Z^1$ is H, OH, an alkyl, epoxy or alkoxy radical, or represents a hydrocarbon radical with at least 4 carbon atoms, which contains one or more hydroxyl group(s) and can be interrupted by one or more oxygen atoms or represents the radical

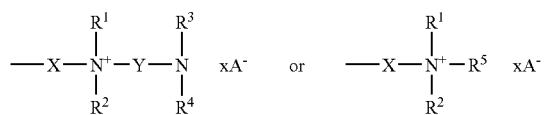

wherein $R^5$ is an alkyl radical with 1 to 20 carbon atoms, $Z^2$ represents the group

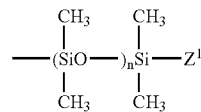

$R^1$, $R^2$,
$R^3$ and
$R^4$ are the same or different and represent alkyl radicals with 1 to 4 carbon atoms or benzyl radicals, or the radicals $R^1$ and $R^3$ or $R^2$ and $R^4$ can be components of a bridging alkylene radical,
$R^6$ represents H or an alkyl radical with 1 to 20 carbon atoms, which can be oxygen-substituted,
E represents the structure —B—O—$(CH_2CH_2O)_v$ $(CH_2CHCH_3O)_wB$—, wherein
B is linear or branched $C_2$ to $C_6$ alkylene,
v 0 to 200,
w 0 to 200,
v+w corresponds to $\geq 1$,
$A^-$ represents an inorganic or organic anion,
n 5 to 200,
m a whole number $\geq 1$ and
s a whole number $\geq 1$.

In a particular embodiment of the polysiloxane polymer of the invention n=5 through 82.

In another special embodiment of the polysiloxane polymers of the invention n=5 through 20.

The polysiloxane compounds pursuant to the invention, especially the formulas (I) and (II), can be used as wash-resistant hydrophilic softening agents for initial textile finishing and as softening agents in formulations based on non-ionogenic or anionic/non-ionogenic surfactants for washing fibers and textiles.

In a preferred embodiment of the present invention, X represents a radical from the group

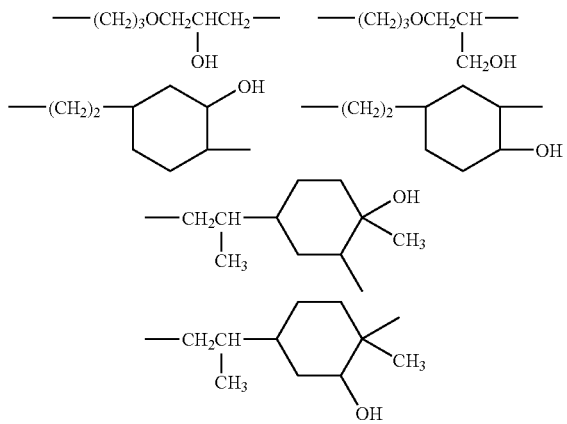

wherein binding to the polysiloxane unit occurs from the left.

In another embodiment of the present invention Y represents a radical $(CH_2)_o$—, with o from 2 to 6.

In another preferred embodiment of the present invention the radicals $R^1$, $R^2$, $R^3$ and $R^4$ represent methyl radicals.

In another preferred embodiment of the present invention $R^6$ represents the structure —$CH_2CH_2OH$, —$CH_3$ or hydrogen. Particularly preferred is $R^6$ as hydrogen.

The group E in the polysiloxane compounds pursuant to the invention is represented by the structure —B—O—$(EOx)_v(POx)_w$—B—, wherein EOx represents an ethyleneoxide unit and POx a propyleneoxide unit. The group —$(EOx)_v(POx)_w$— can moreover represent polyethylene oxide polymer groups, polypropyleneoxide polymer groups and polyethylene oxide-polypropylene oxide copolymer groups. The polyethylene oxide-polypropylene oxide copolymer groups can be statistical or block-like copolymer groups. Particularly preferred are polyethylene oxide-polypropylene oxide block copolymer groups with random arrangement of at least one polyethyleneoxide group and at least one polypropylene oxide group. The latter are especially included in diamines commercially available under the name Jeffamine.

In another preferred embodiment of the present invention B represents —$CH_2CH_2$— and —$CH_2CH(CH_3)$— units.

In a further preferred embodiment of the present invention v represents a range from 0 to 100, preferably 0 to 70, and particularly preferred 0 to 40.

In another preferred embodiment of the present invention w represents a range from 0 to 100, preferably 0 to 70, particularly preferred 0 to 40.

In a further embodiment of the present invention, the ratio $m/(m+s)\times 100$ in the general formulas (I) and (II) is 0.1 to 99.9%. The ratio $m/(m+s)\times 100$ represents the percentage of the number of repetition units of the formula

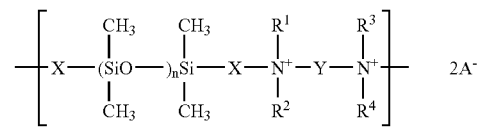

to the total number of repetition units of

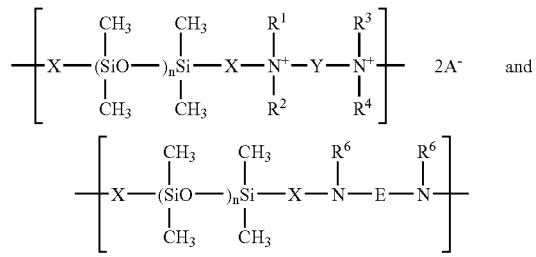

in the polysiloxane polymer pursuant to the invention.

In other words, in the polysiloxane polymer of the invention, the ratio of the number of repetition units of the formula

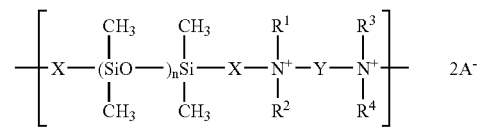

to the number of repetition units of the formula

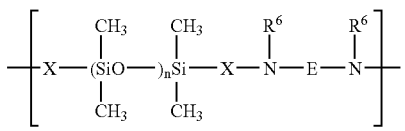

is appropriately around 1:1000 to around 1000:1, preferably 1:1 to 100:1, particularly preferred is 4:1 to 20:1, and even more preferred is 3:1 to 10:1, the most preferred being 3:1 to 9:1.

Through appropriate selection of the above ratio of the repetition units, the properties of the invented polysiloxane, such as for example substantivity (shrinking behavior) in relation to the substrates to be treated, e.g. cellulose fibers, hairs, polyamide fibers, polar paint or plastic surfaces etc., can be controlled and adjusted. Furthermore the washing out behavior, solubility in detergent mixtures or surfactant solutions can be controlled in part with above-mentioned ratio and be adapted to the detergent formulations.

The invented polysiloxanes' additional properties can be influenced by controlling the molecular weight, which in turn can be controlled for example by the addition of monoamines of the formula

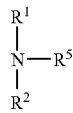

wherein $R^1$, $R^2$ and $R^5$ are as defined above, wherein the above-described definitions can be equal to or different from those of the remaining groups $R^1$, $R^2$ in the molecule, while polymerization can be controlled in the familiar manner. Preferred monoamines are for example trimethylamine, triethylamine, tripropylamine, tributylamine or benzyldimethylamine.

In a preferred embodiment, monoamines are used as chain terminators. If monoamines of the above formula are used as chain terminators, their percentage, in molar terms, amounts for example to a maximum of 20%, 10%, 5% or 1% of the content of di-functional amine repetition units of above-mentioned formulas, resulting for example in a corresponding range of 1 to 20%.

The anion A is preferably represented by physiologically acceptable inorganic radicals, such as chloride, bromide, hydrogen sulfate, sulfate, etc. or organic radicals from the group consisting of acetate, propionate, octanoate, decanoate, dodecanoate, tetradecanoate, hexadecanoate, octadecanoate, oleate.

Another object of the present invention is a method for preparing the polysiloxane compounds pursuant to the invention, characterized by the fact that bisepoxy-terminated polysiloxanes of the formula

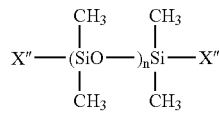

with X″ a bivalent hydrocarbon radical with at least 4 carbon atoms, which contains an epoxy group and which can be interrupted by an oxygen atom, are converted with bis amines of the formula

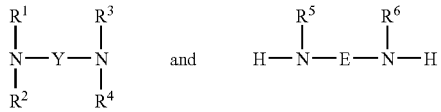

in suitable sequence, possibly while adding a monoamine of the formula

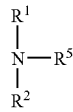

wherein the substituents are as defined above. The invention also relates to the polysiloxane compounds, which can be obtained pursuant to the above method.

In a preferred embodiment of the method of the invention for preparing the polysiloxane compounds of the invention, especially of the general formulas (I) and (II), the starting point for the synthesis are α,ω-Si—H functionalized siloxanes of the general structure

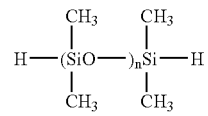

wherein n is defined above.

If not commercially available, these siloxanes can be produced with familiar methods, e.g. through equalization (Silicone, Chemie und Technologie [Silicones, Chemistry and Technology], Vulkan Publishing House, Essen, Germany 1989, p. 82–84).

Initially reactive epoxy-modified intermediate products are produced through hydrosilylation, which can be alkylated in a subsequent step. Suitable starting substances for producing reactive intermediate stages are epoxy-functional alkenes, for example vinylcyclohexeneoxide and allylglycide-ether. The general implementation of hydrosilylation with representatives of the above-mentioned substance group is also known (B. Marciniec, Comprehensive Handbook on Hydrosilylation, Pergamon Press, Oxford, 1992, p. 127–130).

In a subsequent step, the epoxy-modified intermediate stages are then brought to react together with di-tertiary amines and alkylene oxide derivatives preferably bearing two primary or secondary amino functions. The decisive factor here is that an overall stoichiometry of 1:1 of the epoxy groups to the Σ(primary+secondary+tertiary) of the amino groups is maintained. Preferably equimolar HA acid is used for the portion of tertiary amino groups.

Amino-modified alkylene-oxide derivatives usefully exhibit the structure

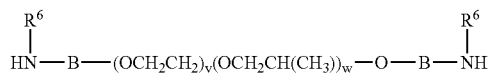

Preferred are here ethylene-oxide-propylene-oxide block copolymers.

Such amines are available commercially under the name Jeffamine® (Huntsman Corp.). A preferred example is represented by

wherein a+b=2–20 c=1–100.

That is, the invented polysiloxane compounds can usefully be produced by converting bisepoxy-terminated polysiloxane compounds with diamines of the formula

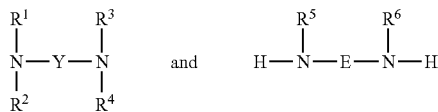

preferably in the presence of acids and possibly in the presence of monoamines of the formula

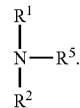

In a preferred method for producing the polysiloxane compounds of the invention, particularly of the formulas (I) and (II), α,ω Si—H functionalized siloxanes of the general structure

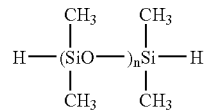

with terminal olefinic bonds, referred to SiH groups 1.0 to 1.5 mol of an epoxy, wherein the epoxy contains at least 4 carbon atoms and can additionally contain a non-cyclic ether groups, are converted in the presence of a hydrosilylation catalyst at temperatures of 50 to 150° C., the excess of olefinic epoxy may possibly be removed, and the reaction product is converted with a mixture of a di-tertiary amine of the formula

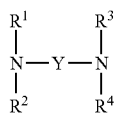

and an alkylene-oxide modified diamine of the structure

in the presence of HA acids at 40 to 120° C., wherein the molar ratio of the epoxy groups to tertiary amino groups to HA acids is a ratio of 1:1:1 and the overall stoichiometry of epoxy groups to the total of (primary+secondary+tertiary) amino groups is also 1:1. The invention also relates to the polysiloxane compounds, which can be obtained pursuant to the above-described method.

In a preferred embodiment of the method for producing the polysiloxane compounds of the invention, particularly of the formulas (I) and (II), the molar ratio of the epoxy groups to the (primary+secondary+tertiary) sum of the amino groups and to the HA acids is 1:1:1.

In a preferred embodiment of the method for producing the polysiloxane compounds pursuant to the invention, especially of the formulas (I) and (II), the species carrying the different amino groups and an equimolar amount of HA acid are jointly added to the mixture.

Although the use of corresponding diamino derivatives is preferred, partially also similar tri-functional or monofunctional structures can be used when a proportional cross-linkage or chain termination is intended. The percentage of tri-functional, cross-linking or mono-functional, chain-terminating amino derivatives in molar terms is 10% maximally, preferably 5%, and particularly preferred is 1% of the content of di-functional derivative.

It is also within the framework of the invention to replace the di-tertiary amine proportionally with monofunctional tertiary amines. Their percentage in molar terms also amounts maximally to 10%, preferably to 5%, particularly preferred 1% of the content of di-tertiary amine.

With regard to conducting the reaction, it is within the framework of the invention to add the HA acid beyond the extent required for quarternization of the tertiary amino groups up to the molar equivalence with all amino groups. This means that the compounds of the invention with regard to the structure of the amino groups can exist as free amines or amine salts so that for example in the case of complete protonation (two additional equivalents of acid) the polysiloxane compounds contain repetition units of the following formula:

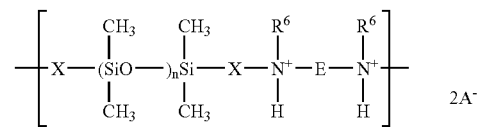

In a preferred variation of the embodiment, the species carrying the different amino groups can be added jointly to the mixture, possibly while adding equimolar amounts of HA acid. However it is also within the framework of the invention initially to react the epoxy derivatives with the tertiary amines in the presence of an HA acid amount equivalent to the tertiary amino groups and subsequently to add the alkylene-oxide derivatives containing the primary or secondary amino groups, possibly while adding HA acid up to equivalence with the amino groups. Finally it is also possible to allow initially the alkylene-oxide derivatives carrying the primary or secondary amino groups, possibly in the presence of equimolar amounts of HA acid, to react with the epoxy derivatives and to then perform the quarternization process.

Furthermore it is in accordance with the invention to cause several siloxane components and/or alkylene-oxide derivatives of different chain lengths to react while maintaining the desired overall stoichiometry. This offers e.g. the possibility of adjusting a desired siloxane chain length by using a single siloxane component or through the specific mixture of several siloxane components. Similarly it is also possible to represent a beneficial average alkylene oxide block length in the form of a monomodal, bimodal or polymodal distribution.

The quarternization and alkylation reactions are preferably performed in polar organic solvents. Suitable are e.g. alcohols from the group of methanol, ethanol, i-propanol and n-butanol; glycols from the group of ethyleneglycol, di-ethyleneglycol, tri-ethyleneglycol, the methyl, ethyl and butyl ethers of the above-mentioned glycols, 1,2-propylene glycol and 1,3-propylene glycol, ketones such as acetone and methylethyl ketone; esters from the group of ethylacetate, butylacetate and 2-ethyl-hexylacetate, such as tetrahydrofuran and nitro compounds such as nitromethane. The selection of the solvent essentially depends on the solubility of the reaction partners and the desired reaction temperature. The reactions are executed preferably in the range from 20° C. to 150° C., and particularly in the range from 40° C. to 100° C.

EP-A-0 282 720 deals with the use of polyquaternary polysiloxanes in cosmetic formulations, specifically for treating hair. Benefits that are mentioned include an improved ability to comb the hair, good shine, high antistatic effectiveness and improved washout resistance.

The last-mentioned property cannot be equated with the wash-resistant characteristic in the sense of the invention. While washout resistance out of hair refers to the short-term effect of primarily water and very mild surfactants that do not irritate the Skin, wash-resistant, hydrophilic softening agents for textiles must withstand the effects of concentrated surfactant solutions with high fat- and dirt-solving ability. In modern detergents, strong alkaline complexing agents, oxydatively acting bleaching agents and complex enzyme systems are added to these surfactant systems. They are allowed to act frequently for hours at elevated temperatures. For these reasons it is impossible to translate the experiences from the cosmetic field to the field of wash-resistant textile softening agents. DE-OS 32 36 466 quoted in the state of the art shows that cross-linkable systems should be the focus when trying to achieve a wash-resistant textile system.

Similarly it was not to be expected that the compounds pursuant to the invention can be effective as softening agents in formulations based on non-ionic or anionic/non-ionic surfactants. In these cases as well the aggressive detergent formulations are allowed to act for long periods of time at elevated temperatures. An additionally aggravating factor is that the modification of the fiber surface with softening substances beforehand is eliminated.

The invention furthermore relates to the use of the above-described polysiloxane compounds in cosmetic formulations for skin and hair care, in polishes for treating and finishing hard surfaces, in formulations for drying automobiles and other hard surfaces, for example after power washing, for finishing textiles and textile fibers, as separate softening agents after washing textiles with non-ionogenic or anionic/non-ionogenic detergent formulations, as softening agents in formulations based on non-ionic or anionic/non-ionic surfactants, as well as means for preventing or undoing textile wrinkling.

The invention furthermore relates to the use of the above-described polysiloxane compounds as wash-resistant hydrophilic softening agents for textile finishing.

Furthermore the invention relates to compositions, which contain at least one of the polysiloxane compounds together with at least one additional substance common for the composition.

The following lists some typical examples of such compositions, in which the polysiloxane compounds of the invention can be used beneficially.

Typical auxiliary agents in such compositions are e.g. such substances, which are described in A. Domsch: Die kosmetischen Präparate [Cosmetic Preparations], Vol. I and II, 4$^{th}$ Edition, Publishing House for the Chemical Industry, H. Ziolkowsky K G, Augsburg, as well as International Cosmetic Ingredient Dictionary and Handbook, 7$^{th}$ Edition 1997 by J. A. Wenniger, G. N. McEwen, Vol. 1–4 by The Cosmetic, Toiletry and Fragrance Association, Washington, D.C. or under http://www.cosmetic-world.com/inci/lncialf.htm.

Anionic Shampoo:

The formulation example should be interpreted as a basic formulation. Anionic shampoo generally contains the following components, without being limited to them:

Alkyl sulfates, alkyl ether sulfates, sodium lauryl sulfate, sodium lauryl ether sulfate, ammonium lauryl sulfate, ammonium lauryl ether sulfate, TEA lauryl sulfate, TEA lauryl ether-sulfate, alkylbenzene sulfonates, α-olefin sulfonates, paraffin sulfonates, sulfosuccinate, N-acyl taurides, sulfate glycerides, sulfated alkanolamides, carboxylate salts, N-acyl-amino acid salts, silicones, etc.

| Component | % |
| --- | --- |
| Ammonium lauryl sulfate | 10.00–30.00 |
| Ammonium lauryl ether sulfate | 5.00–20.00 |
| Cocamidopropyl betaine | 0.00–15.00 |
| Lauramid DEA | 0.00–5.00 |
| Cocamide Mea | 0.00–5.00 |
| Dimethicone copolyol (dimethyl siloxane glycol polymer) | 0.00–5.00 |
| Cyclopentasiloxanes | 0.00–5.00 |
| Polysiloxane compound of the invention | 0.50–5.00 |
| Polyquaternium-10 | 0.00–2.00 |
| Preservatives | 0.00–0.50 |
| Aromas | 0.00–5.00 |
| Deionized water | q.s. 100% |
| Sodium chloride | q.s. |

Nonionic Shampoo

The formulation example is intended to serve as a basic formulation. Nonionic shampoos typically include, but are not limited to, the following components: monoalkanolamides, monoethanolamides, monoisopropanolamides, polyhydroxy derivatives, sucrose monolaurate, polyglycerine ether, aminoxides, polyethoxylated derivatives, sorbitan derivatives, silicones, etc.

| Component | % |
| --- | --- |
| Lauramid DEA | 10.00–30.00 |
| Lauramid oxide | 5.00–20.00 |
| Cocamide Mea | 0.00–5.00 |
| Dimethicone Copolyol | 0.00–5.00 |
| Polysiloxane compound of the invention | 0.50–5.00 |
| Preservatives | 0.00–5.00 |
| Aromas | 0.00–5.00 |
| Deionized water | q.s. 100% |
| Sodium chloride | q.s. |

Amphoteric Shampoo

The formulation example is intended to serve as a basic formulation. Formulations of this category typically include, but are not limited to, the following components:

N-alkyl iminodipropionates, N-alkyl iminopropionates, amino acids, amino acid derivatives, amidobetaines, imidazolinium derivatives, sulfobetaines, sultaines, betaines, silicones, etc.

| Component | % |
| --- | --- |
| PEG-80 sorbitan laurate | 10.00–30.00 |
| Lauroamphoglycinate | 0.00–10.00 |
| Cocamidopropyl hydroxysultaine | 0.00–15.00 |
| PEG-150 distearate | 0.00–5.00 |
| Laurylether-13-carbocylate | 0.00–5.00 |
| Polysiloxane compound of the invention | 0.50–5.00 |
| Aromas | 0.00–5.00 |
| Deionized water | q.s. 100% |
| Sodium chloride | q.s. |

Cationic Shampoo

The formulation example is intended to serve as a basic formulation. Formulations of this category typically include, but are not limited to, the following components: Biquarternary ammonium compounds. Bi-(trialkylammoniumacetyl)diamines, amidoamines, ammonioalkyl ester, silicones. etc.

| Compound | % |
| --- | --- |
| Laurylether-13-carboxylate | 10.00–30.00 |
| Isopropyl myristate | 5.00–20.00 |
| Cocamidopropyl betaine | 0.00–15.00 |
| Lauramid DEA | 0.00–5.00 |
| Cocamide MEA | 0.00–5.00 |
| Polysiloxane compound of the invention | 0.50–5.00 |
| Preservatives | 0.00–0.50 |
| Aromas | 0.00–5.00 |
| Deionized water | q.s. 100% |
| Sodium chloride | q.s. |

Solidifying Agents

The formulation example is intended to serve as a basic formulation. Formulations of this category typically include, but are not limited to, the following components: Fatty acids, fatty acid esters, ethoxylated fatty acids, ethoxylated fatty acid esters, fatty alcohols, ethoxylated fatty alcohols, glycols, glycol esters, glycerin, glycerin ester, lanolin, lanolin derivatives, mineral oil, petroleum jelly, lecithin, lecithin derivatives, waxes, wax derivatives, cationic polymers, proteins, protein derivatives, amino acids, amino acid derivatives, humectants, thickening agents, silicones, etc.

| Component | % |
| --- | --- |
| Ceteareth-20 | 0.10–10.00 |
| Steareth-20 | 0.10–10.00 |
| Stearyl alcohol | 0.10–10.00 |
| Stearamidopropyl dimethylamine | 0.00–10.00 |
| Dicetyldimonium chloride | 0.00–10.00 |
| Polysiloxane compound of the invention | 0.50–5.00 |
| Cyclopentasiloxane | 0.00–5.00 |
| Dimethicones | 0.00–5.00 |
| Preservatives | 0.00–0.50 |
| Aromas | 0.00–5.00 |
| Deionized water | q.s. 100% |

"Clear Rinse-Off" Solidifying Agents

The formulation example is intended to serve as a basic formulation. Formulations of this category typically include, but are not limited to, the following components: Fatty acids, fatty acid esters, ethoxylated fatty acids, ethoxylated fatty acid esters, fatty alcohols, ethoxylated fatty alcohols, glycols, glycol esters, glycerin, glycerin ester, lanolin, lanolin derivatives, mineral oil, petroleum jelly, lecithin, lecithin derivatives, waxes, wax derivatives, cationic polymers, proteins., protein derivatives, amino acids, amino acid derivatives, humectants, thickening agents, silicones, etc.

| Component | % |
| --- | --- |
| Glycerin | 0.10–10.00 |
| Cetrimonium chloride | 0.00–10.00 |
| Polysiloxane compound of the invention | 0.50–5.00 |
| Hydroxyethyl cellulose | 0.00–5.00 |
| Preservatives | 0.00–0.50 |
| Aromas | 0.00–5.00 |
| Deionized water | q.s. 100% |

Foam Solidifying Agents for Hair

The formulation example is intended to serve as a basic formulation. Formulations of this category typically include, but are not limited to, the following components: Fatty acids, fatty acid esters, ethoxylated fatty acids, ethoxylated fatty acid esters, fatty alcohols, ethoxylated fatty alcohols, glycols, glycol esters, glycerin, glycerin ester, lanolin, lanolin derivatives, mineral oil, petroleum jelly, lecithin, lecithin derivatives, waxes, wax derivatives, cationic polymers, proteins, protein derivatives, amino acids, amino acid derivatives, humectants, thickening agents, silicones, solvents, ethanol, isopropyl, isoparaffin solvent, butane, propane, isobutane, CFCs, fluorinated aerosol propellants, dimethyl ether, compressed gases, etc.

| Component | % |
| --- | --- |
| Polysiloxane compound of the invention | 0.50–5.00 |
| Nonoxynol-15 | 0.00–2.00 |
| Nonoxynol-20 | 0.00–2.00 |
| Aromas | 0.00–5.00 |
| Aerosol propellants | 0.00–20.00 |
| Preservatives | 0.00–0.50 |
| Deionized water | q.s. 100% |

Pump Spray (Solidifying Agent) for Hair

The formulation example is intended to serve as a basic formulation. Formulations of this category typically include, but are not limited to, the following components: Fatty acids, fatty acid esters, ethoxylated fatty acids, ethoxylated fatty acid esters, fatty alcohols, ethoxylated fatty alcohols, glycols, glycol esters, glycerin, glycerin ester, lanolin, lanolin derivatives, mineral oil, petroleum jelly, lecithin, lecithin derivatives, waxes, wax derivatives, cationic polymers, proteins, protein derivatives, amino acids, amino acid derivatives, humectants, thickening agents, silicones, solvents, ethanol, isopropyl, isoparaffin solvent, etc.

| Component | % |
| --- | --- |
| Polysiloxane compound of the invention | 0.50–5.00 |
| Cyclomethicones | 0.00–80.00 |
| Ethanol | 0.00–80.00 |
| Preservatives | 0.00–0.50 |
| Aromas | 0.00–5.00 |
| Deionized water | q.s. 100% |

Solidifying Agent Spray for Hair

The formulation example is intended to serve as a basic formulation. Formulations of this category typically include, but are not limited to, the following components: Fatty, acids, fatty acid esters, ethoxylated fatty acids, ethoxylated fatty acid esters, fatty alcohols, ethoxylated fatty alcohols, glycols, glycol esters, glycerin, glycerin ester, lanolin, lanolin derivatives, mineral oil, petroleum jelly, lecithin, lecithin derivatives, waxes, wax derivatives, cationic polymers, proteins, protein derivatives, amino acids, amino acid derivatives, humectants, thickening agents, silicones, solvents, ethanol, isopropyl, isoparaffin solvent, butane, propane, isobutane, CFCs, fluorinated aerosol foaming agents, dimethyl ether, compressed gases, etc.

| Component | % |
| --- | --- |
| Polysiloxane compound of the invention | 0.50–5.00 |
| Cyclomethicones | 0.00–80.00 |
| Ethanol | 0.00–50.00 |

-continued

| Component | % |
|---|---|
| Aerosol foaming agents | 0.00–50.00 |
| Preservatives | 0.00–0.50 |
| Aromas | 0.00–5.00 |
| Deionized water | q.s. 100% |

Solidifying Agent Gel for Hair

The formulation example is intended to serve as a basic formulation. Formulations of this category typically include, but are not limited to, the following components: Thickening agents, cellulose derivatives, acrylic acid derivatives, fixative polymers, conditioning chemicals, glycols, glycol ester, glycerin, glycerin ester, lanolin, lanolin derivatives, mineral oil, petroleum jelly, lecithin, lecithin derivatives, waxes, wax derivatives, cationic polymers, proteins, protein derivatives, amino acids, amino acid derivatives, humectants, silicones, solvents, ethanol, isopropyl, isoparaffin solvents, etc.

| Component | % |
|---|---|
| Polysiloxane compound of the invention | 0.50–5.00 |
| Hydroxyethyl cellulose | 0.00–2.00 |
| Aromas | 0.00–5.00 |
| Preservatives | 0.00–0.50 |
| Citric acid | 0.00–2.00 |
| Deionized water | q.s. 100% |

Styling Gel for Hair

The formulation example is intended to serve as a basic formulation. Formulations of this category typically include, but are not limited to, the following components: Fixative polymers, lacquers, acrylic acid derivatives, cellulose derivatives, vinyl derivatives, conditioning chemicals, glycols, glycol ester, glycerin, glycerin ester, lanolin, lanolin derivatives, mineral oil, petroleum jelly, lecithin, lecithin derivatives, waxes, wax derivatives, cationic polymers, proteins, protein derivatives, amino acids, amino acid derivatives, humectants, thickening agents, silicones, solvents, ethanol, isopropyl, isoparaffin solvents, etc.

| Component | % |
|---|---|
| Polysiloxane compound of the invention | 0.50–5.00 |
| Fixatives | 0.10–10.00 |
| Hydroxyethyl cellulose | 0.00–2.00 |
| Aromas | 0.00–5.00 |
| Citric acid | 0.00–2.00 |
| Deionized water | q.s. 100% |

Styling Spray for Hair

The formulation example is intended to serve as a basic formulation. Formulations of this category typically include, but are not limited to, the following components: Fixative polymers, lacquers, vinyl derivatives, fatty acids, fatty acid esters, ethoxylated fatty acids, ethoxylated fatty acid esters, fatty alcohols, ethoxylated fatty alcohols, glycols, glycol esters, glycerin, glycerin ester, lanolin, lanolin derivatives, mineral oil, petroleum jelly, lecithin, lecithin derivatives, waxes, wax derivatives, cationic polymers, proteins, protein derivatives, amino acids, amino acid derivatives, humectants, thickening agents, silicones, solvents, ethanol, isopropyl, isoparaffin solvent, butane, propane, isobutane, CFCs, fluorinated aerosol propellants, dimethyl ether, compressed gases, etc.

| Component | % |
|---|---|
| Polysiloxane compound of the invention | 0.50–5.00 |
| Cyclomethicones | 0.00–80.00 |
| Fixatives | 0.10–10.00 |
| Ethanol | 0.00–50.00 |
| Aerosol propellants | 0.00–50.00 |
| Preservatives | 0.00–0.50 |
| Aromas | 0.00–5.00 |
| Deionized water | q.s. 100% |

Pump Spray (Styling) for Hair

The formulation example is intended to serve as a basic formulation. Formulations of this category typically include, but are not limited to, the following components: Vinyl derivatives, fixative polymers, lacquers, fatty acids, fatty acid esters, ethoxylated fatty acids, ethoxylated fatty acid esters, fatty alcohols, ethoxylated fatty alcohols, glycols, glycol esters, glycerin, glycerin ester, lanolin, lanolin derivatives, mineral oil, petroleum jelly, lecithin, lecithin derivatives, waxes, wax derivatives, cationic polymers, proteins, protein derivatives, amino acids, amino acid derivatives, humectants, thickening agents, silicones, solvents, ethanol, isopropyl, isoparaffin solvent, butane, propane, isobutane, CFCs, fluorinated aerosol propellants, dimethyl ether, compressed gases, etc.

| Component | % |
|---|---|
| Polysiloxane compound of the invention | 0.50–5.00 |
| Fixatives | 0.10–10.00 |
| Cyclomethicones | 0.00–80.00 |
| Ethanol | 0.00–50.00 |
| Preservatives | 0.00–0.50 |
| Aromatic essences | 0.00–5.00 |
| Deionized water | q.s. 100% |

Use of the polysiloxane derivatives pursuant to the invention in hair care leads to positive effects with respect to fixation, shine, hold, body, volume, moisture regulation, color retention, protection from environmental influences (UV, salt water, etc.), manageability, antistatic properties, dyeability etc.

EXAMPLES

The following Examples serve to explain the invention in more detail without limiting it.

Example 1

1a) 24 g water and 4.18 g (0.048 mol tertiary amino groups) N,N,N'-tetramethyl-1,6-hexandiamine and 12.77 g (0.012 mol primary amino groups) of an alkylene oxide derivative known under the trade name Jeffamin® ED 2003 with the structure

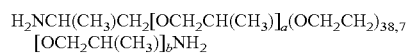

with a+b=6 were placed in a 1 liter three-necked flask at room temperature. Within 5 minutes 12.0 g (0.03 mol) of dodecanoic acid was added in the form of a 50% solution in 2-propanol and 1.8 g (0.03 mol) acetic acid. After the batch was heated to 50° C., 194.1 g (0.06 mol epoxy groups) of an epoxy siloxane with the following average composition

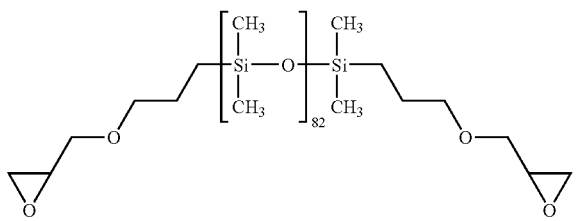

and 30 ml 2-propanol were added drop by drop within 30 minutes. The yellow, turbid mixture was heated to reflux temperature for 6 hours. Once all the matter volatile at temperatures up to 100° C. and at 2 mmHg in a vacuum are removed, 209 g of a beige, cloudy material with the following structure

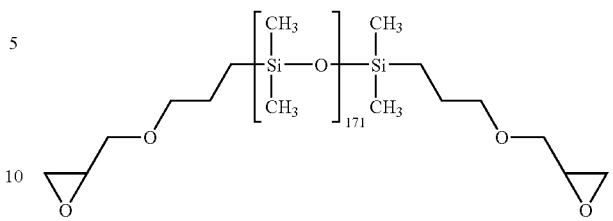

0.05 mol dodecanoic acid, and
0.05 mol acetic acid.
and the trimethyl amine-terminated polysiloxane is isolated.

Example 2

To prove that the substance is suitable for use as a wash resistant hydrophilic softener, white cotton jersey was subjected to the following treatment with a formulation based on the quarternary ammonium salt pursuant to Example 1. A commercially available hydrophilic softener HSSD Magnasoft® by Osi Specialties was used as reference. To begin with, the following clear master formulations were prepared:

remain. Thereby the above formula must be understood such that it is a statistic copolymer, the molar ratio of the two amines being 0.8 to 0.2.

| 13C-NMR: Substructure | Shift (ppm) |
|---|---|
| —$\underline{C}$H(OH)—CH$_2$—N$^+$[(CH$_3$)$_2$]—CH$_2$—CH$_2$— | 65.4 |
| —CH(OH)—$\underline{C}$H$_2$—N$^+$[(CH$_3$)$_2$]—CH$_2$—CH$_2$— | 64.1 |
| —CH(OH)—CH$_2$—N$^+$[($\underline{C}$H$_3$)$_2$]—CH$_2$—CH$_2$— | 52.3/52.5 |
| —CH(OH)—CH$_2$—N$^+$[(CH$_3$)$_2$]—$\underline{C}$H$_2$—CH$_2$— | 63.8 |
| —CH(OH)—CH$_2$—N$^+$[(CH$_3$)$_2$]—CH$_2$—$\underline{C}$H$_2$— | 23.4 |
| —$\underline{C}$H$_2$—O—CH$_2$— | 70.6 |

Example 1a

A trimethylamine-terminated polysiloxane is converted in a manner analogous to Example 1 by the transformation of 0.08 mol tetramethylhexamethylendiamine,
0.01 mol Jeffamine ED 2003,
0.02 mol trimethylamine,
0.1 mol of a diepoxide with the formula

|  | Reference Product |
|---|---|
| Example 1 | Magnasoft ® HSSD |
| 20.0 g Example 1 | 20.0 g siloxane softener |
| 0.4 g acetic acid | 0.2 g acetic acid |
| 74.6 g dist. water | 79.8 g dist. water |
| 5.0 g Renex 36 ® (Henkel) | |

Of said master formulation, 20 g was dissolved in 980 g distilled water. Then 60 cm×90 cm cotton jersey pieces weighing 87 g were finished with these formulations containing effectively 0.4% siloxane agent using the Foulard method. To that end the cotton material was completely submerged in the respective formulation for 5 to 10 seconds and dried for 3 minutes at 120° C. following a forced application.

Then the rags were divided in half and one half was subjected to five machine wash cycles in the presence of a detergent for fine fabrics (1.7 g detergent/liter washing solvent). Every wash cycle lasted 25 minutes; the wash temperature was 40° C.

Based on the unwashed and washed fabric pieces the hydrophilicity (soak-in time of a drop of water in seconds) was determined and the hand was evaluated by 10 test persons.

|  | Hydrophilism | Hand |
| --- | --- | --- |
| Example 1 finished; unwashed | <3 | Smooth, flat, soft |
| Example 1 finished; washed 5× | <2 | Smooth, flat, medium soft |
| Reference material; unwashed | 1 | Smooth, flat |
| Reference material; washed 5× | 1 | Hard |

The results showed that even after 5 wash cycles the textile material finished pursuant to the invention still possesses the desired combination of properties, i.e. hydrophilicity demonstrated by a very short soak-in time for drops as well as the hand typical of silicone.

Example 3

To prove the softening properties as an internal softener during the wash process, bleached cotton strips with unfinished surfaces were subjected to a wash cycle in the presence of Ariel Futur®, bentonite-containing Dash 2 in 1® as well as the compound described under Example 1. The following marginal conditions were maintained.

|  | Strip 1 | Strip 2 | Strip 3 |
| --- | --- | --- | --- |
| Strip weight (g) | 12.94 | 13.00 | 13.10 |
| Water volume (ml) | 641 | 653 | 670 |
| Detergent | 0.64 g Ariel Futur® | 0.65 g Ariel Futur® | 0.66 g Dash 2 in 1® |
| Polysiloxane compound Emb. 1 | 0.2 g | — | — |
| Grade average | 1.3 | 2.9 | 1.8 |

The water was heated to 60° C., the detergents—and, in the case of cotton strip no. 1 the compound pursuant to Example 1 as well—dissolved. Then the cotton strips were laundered in those solutions for 30 minutes. Afterwards the strips were rinsed five times with 600 ml water and then dried for 30 minutes at 120° C.

16 test persons evaluated the cotton strips with respect to the softness of the hold, the grade 1 being reserved for the softest strip and the grade 3 for the strip considered to be the hardest.

The evaluation result was such that the cotton strip no. 1 obtained the average grade 1.3, the cotton strip no. 2 the average grade 2.9 and the strip no. 3, which was treated with betonite, the Grade 1.8.

What is claimed is:

1. Polysiloxane polymers having the repeating units

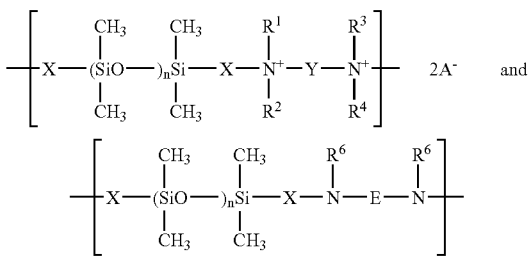

wherein

X is a divalent hydrocarbon radical with at least 4 carbon atoms, which contains a hydroxyl group and which carbon atoms optionally are interrupted by an oxygen atom, and wherein the X groups are the same or different in the repeating units, Y is a divalent hydrocarbon radical having at least 2 carbon atoms, which optionally comprises a hydroxyl group and in which the carbon atoms are optionally interrupted by one or more oxygen or nitrogen atoms, $R^1$, $R^2$, $R^3$ and $R^4$ are the same or different and represent alkyl groups of 1 to 4 carbon atoms or benzyl groups, or the $R^1$ and $R^3$ radicals or the $R^2$ and $R^4$ together form a bridging alkylene radical, $R^6$ is H or an alkyl radical having 1 to 20 carbon atoms, which is optionally oxygen-substituted, E is the structure —B—O—$(CH_2CH_2O)_v(CH_2CHCH_3O)_w$B—, wherein B represents straight chain or branched chain $C_2$ to $C_6$ alkylene, v is a number from 0 to 200, w is a number from 0 to 200, v+w≧1, n represents a number from 2 to 1000, wherein the n's in the repeating units may be the same or different, and $A^-$ represents an inorganic or organic anion.

2. Polysiloxane polymers according to claim 1, wherein said polymers are linear or cyclic polysiloxane polymers.

3. Polysiloxane polymers according to claim 2, wherein said polymers are linear polysiloxane polymers containing terminal groups selected from the group consisting of

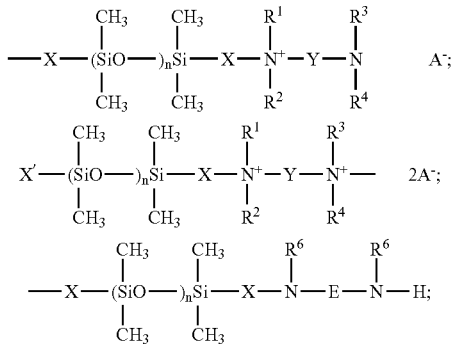

-continued

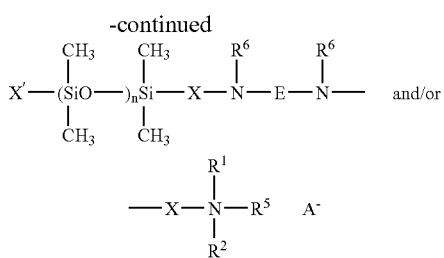

wherein
X' is a hydrocarbon radical having at least 4 carbon atoms, comprising an epoxy group or an epoxy group opened with alcohols, water or amines and said carbon atoms are optionally interrupted by an oxygen atom,
$R^5$ is an alkyl radical having 1 to 20 carbon atoms, and wherein the terminal X groups in the terminal groups bind to the terminal nitrogen atoms of the repeating units, and the terminal nitrogen atoms in the terminal groups bind to the terminal X groups of the repeating units.

4. Polysiloxane polymers according to claim 2, wherein said polymers are cyclic, polyquarternary polysiloxane polymers of the formula (I)

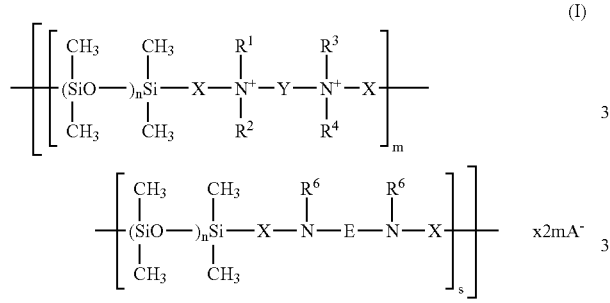

and/or linear compounds of the formula (II)

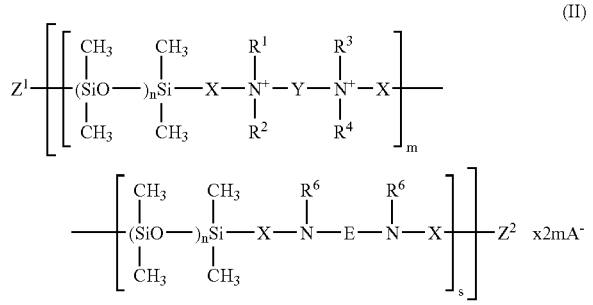

whereby
$Z^1$ is a H, OH, an alkyl, epoxy or alkoxy radical, or a hydrocarbon radical having at least 4 carbon atoms, one or more hydroxyl group(s) and wherein said carbon atoms are optionally interrupted by one or more oxygen atoms, or represents the radical

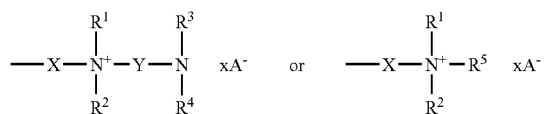

whereby $R^5$ is an alkyl radical having 1 to 20 carbon atoms, $Z^2$ is the group

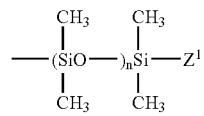

n is a number of from 5 to 200,
m is a whole number $\geq 1$ and
s is a whole number $\geq 1$.

5. Polysiloxane polymers according to claim 4, wherein n=5 to 82.

6. Polysiloxane polymers according to claim 5, wherein n=5 to 20.

7. Polysiloxane polymers according to claim 1, wherein X is a radical selected from the group consisting of

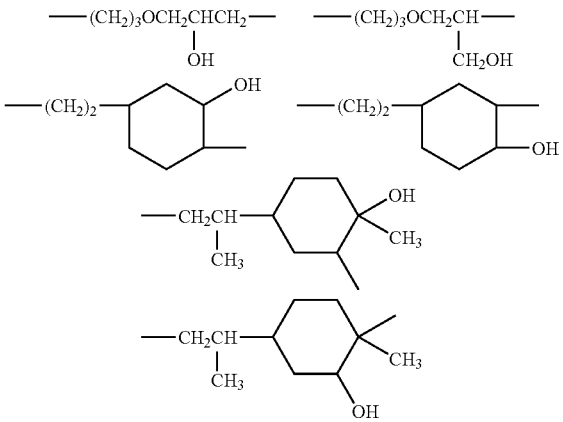

wherein Y is a radical —$(CH_2)_o$—, o is a number from 2 to 6, the groups $R^1$, $R^2$, $R^3$, $R^4$ are methyl radicals, and $R^6$ is hydrogen, —$CH_2CH_2OH$ or —$CH_3$.

8. Polysiloxane polymers according to claim 1, wherein the structural element B is —$CH_2CH_2$— or —$CH_2CH(CH_3)$—.

9. Polysiloxane polymers according to claim 1, wherein the Y is —$(CH_2)_o$—, where o is a number from 2 to 6.

10. Polysiloxane polymers according to claim 1, wherein $R^1$, $R^2$, $R^3$, and $R^4$ are methyl.

11. Polysiloxane polymers according to claim 1, wherein $R^6$ is hydrogen, —$CH_2CH_2OH$—, or —$OH_3$.

12. Polysiloxane polymers according to claim 1, wherein v is 0 to 100.

13. Polysiloxane polymers according to claim 4, wherein m/(m+s)×100=0.1 to 99.9%.

14. Polysiloxane polymers according to claim 1, wherein w stands for 0 to 100.

15. Polysiloxane polymers according to claim 1, wherein $A^-$ is an anion selected from the group consisting of chloride, bromide, hydrogen sulfate, sulfate, acetate, propionate, octanoate, decanoate, dodecanoate, tetradecanoate, hexadecanoate, octadecanoate and oleate.

16. Polysiloxane polymers according to claim 1, in the form of a protonated amine salts.

17. Method for the production of the polysiloxane polymers of claim 1, wherein bis epoxide-terminated polysiloxanes of the formula

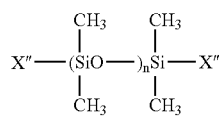

wherein X″ is a divalent hydrocarbon group with at least 4 carbon atoms, which comprises an epoxy group and wherein said carbon atoms are optionally interrupted by an oxygen atom, are converted with bis amines of the formula

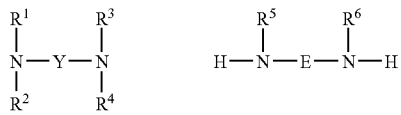

optionally by adding a monoamine of the formula

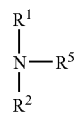

whereby the substitutes have the meanings given in claim 1.

18. Hydrophilic softeners on the basis of quarternary siloxanes containing ammonium groups, wherein said siloxanes are the polysiloxane polymers of claim 1.

19. A wash-resistant hydrophilic softener formulation comprising a polysiloxane polymer of claim 1.

20. A method for the initial finishing of textiles, which comprises finishing said textiles with a wash-resistant hydrophilic softener comprising a polysiloxane polymer of claim 1.

21. Cosmetic skin and hair care formulations, polishes for the treatment and finishing of hard surfaces, formulations for drying cars and other hard surfaces after machine washing, comprising a polysiloxane polymer of claim 1.

22. The softener of claim 19, further comprising a non-ionic or anionic/non-ionic surfactant.

23. A method for laundering textiles, comprising laundering said textiles with a softener formulation of claim 22.

24. A method for finishing textiles or textile fibers after laundering with non-ionic or anionic/non-ionic detergent formulations, wherein said textiles or textile fibers are treated, after laundering with a non-ionic or anionic/non-ionic detergent, with a softener formulation comprising a polysiloxane polymer of claim 1.

25. Polysiloxane polymers according to claim 12 wherein v is 0 to 70 and v+w≧1.

26. Polysiloxane polymers according to claim 12, wherein v is 0 to 40 and V+w≧1.

27. Polysiloxane polymers according to claim 14, wherein w is 0 to 70 and V+w≧1.

28. Polysiloxane polymers according to claim 24, wherein w is 0 to 40 and v+w≧1.

* * * * *